United States Patent [19]
Axelsson

[11] Patent Number: 5,736,022
[45] Date of Patent: Apr. 7, 1998

[54] SPACER

[75] Inventor: Urban Jonsson Axelsson, Alunda, Sweden

[73] Assignee: Pharmacia Biotech AB, Upsala, Sweden

[21] Appl. No.: 750,744

[22] PCT Filed: Jun. 21, 1995

[86] PCT No.: PCT/SE95/00762
§ 371 Date: Dec. 20, 1996
§ 102(e) Date: Dec. 20, 1996

[87] PCT Pub. No.: WO95/35496
PCT Pub. Date: Dec. 28, 1995

[30] Foreign Application Priority Data
Jun. 21, 1994 [SE] Sweden ................... 9402190

[51] Int. Cl.$^6$ ................ G01N 27/26; G01N 27/447
[52] U.S. Cl. ................ 204/467; 204/466; 204/616; 204/618; 204/619
[58] Field of Search ................ 204/618, 619, 204/620, 621, 467, 466, 616

[56] References Cited

U.S. PATENT DOCUMENTS

| 4,518,476 | 5/1985 | Delony et al. | 204/618 |
| 4,675,095 | 6/1987 | Kambara et al. | 204/612 |
| 4,839,016 | 6/1989 | Anderson | 204/616 |
| 5,186,807 | 2/1993 | Sanford et al. | 204/618 |

FOREIGN PATENT DOCUMENTS

| 0334615 | 9/1989 | European Pat. Off. . |
| 0534135 | 3/1993 | European Pat. Off. . |
| 58-103656 | 6/1983 | Japan . |
| WO 87/07719 | 12/1987 | WIPO . |

*Primary Examiner*—Kathryn L. Gorgos
*Assistant Examiner*—John S. Starsiak, Jr.
*Attorney, Agent, or Firm*—Birch, Stewart, Kolasch & Birch, LLP

[57] ABSTRACT

A spacer in the form of an elongated, rectangular parallelepiped for use between the two glass plates of a gel cassette to delimit a space for receiving an electrophoresis gel between the glass plates where the spacer is made of glass.

5 Claims, 1 Drawing Sheet

SPACER

This application is a national stage application of PCT/SE95/00762 filed Jun. 21, 1995 published as WO95/35496 Dec. 28, 1995.

TECHNICAL FIELD

The invention relates to a spacer in the form of an elongated, rectangular parallelepiped for use between the two glass plates of a gel cassette to delimit a space for receiving an electrophoresis gel between the glass plates, an arrangement at a gel cassette having two glass plates which are kept apart by means of at least two spacers to define a space for receiving an electrophoresis gel, said spacers being in the form of elongated, rectangular parallelepipeds, and use of such a gel cassette.

BACKGROUND OF THE INVENTION

From U.S. Pat. No. 4,675,095 such a spacer is known in an electrophoresis apparatus of the fluorescence detection type, where light from an excitation light source is projected from the side into the electrophoresis gel to enable detection of fluorophor labelled fragments in samples that migrate along electrophoretic paths in the gel. From this U.S. patent it is apparent that the spacer is to be transparent with respect to the excitation light. In a commercial embodiment, this spacer is a plastic spacer. A disadvantage of a plastic spacer is that it is very difficult to produce the optical surfaces that are necessary in order to project the excitation light into the gel with high efficiency. Moreover, tensions in the plastic material can give rise to unwanted optical effects. Furthermore, the useful life of such spacers will be very short since the plastic material is easily scratched. Another disadvantage is that the separation medium used is not polymerized homogeneously enough adjacent to plastic spacers upon casting, which causes so called "smiling" and a skew migration of the samples in the gel during an electrophoresis run. Also, a poorly polymerized gel can cause refractions that deflect the excitation light.

An attempt to eliminate these problems is known from WO 87/07719, where the spacers are divided and separate light guides are inserted between the respective spacer parts to guide the excitation light into and out of the gel. In a commercial embodiment the spacer parts are of plastic while the light guides are of glass.

However, the handling of divided spacers of plastic with separate light guides is problematic in view of the fact that a number of separate parts are to be fitted together. The light guides can namely easily end up misaligned and, moreover, sealing problems can appear upon casting of the gel.

BRIEF DESCRIPTION OF THE INVENTION

The object of the invention is to bring about a spacer of the type mentioned in the introductory portion, which does not possess the disadvantages of the spacers known so far.

This is attained by means of the spacer according to the invention in that it is of glass.

PREFERRED EMBODIMENT

Figure 1:
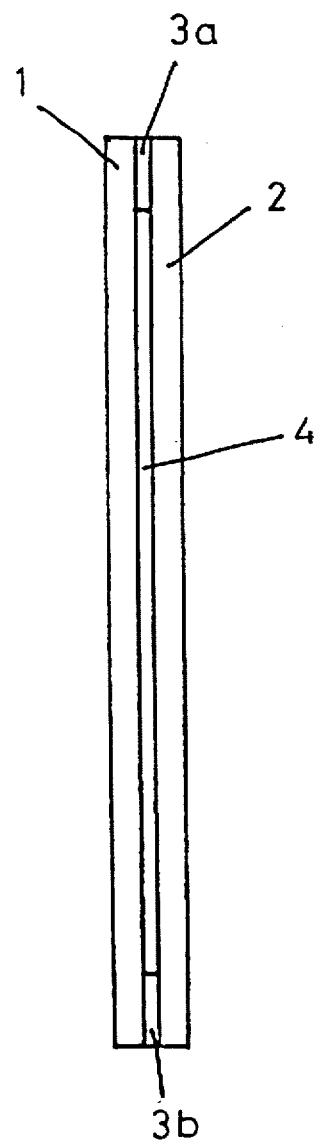
FIG. 1 is an end view of a gel cassette having spacers in accordance with the present invention.

The single figure (FIG. 1) is an end view of a gel cassette having two glass plates 1 and 2, which are kept separate by means of two spacers 3a and 3b according to the invention to delimit, in a manner known per se, a space 4 for receiving an electrophoresis gel (not shown).

The spacers 3a and 3b comprise separate, elongated, rectangular parallelepipeds and, in accordance with the invention, in the gel cassette shown, at least one of the spacers is completely made of glass, e.g. a boron silicate glass, in order for the gel cassette to be usable in electrophoresis apparatuses where excitation light is projected from the side into the gel for automatic direct detection of e.g. fluorephor labelled samples.

By making the spacers 3a and 3b completely of glass a more homogenous polymerization of a gel which is cast in the space 4 between the plates 1 and 2, is obtained in that it polymerizes better against glass than against plastic. In an electrophoresis run this will appear in the form of considerably less so called "smiling" and skew migration of the samples in the gel adjacent to the edges.

Also, in case denaturated gels with urea are used, the improved polymerization causes the amount of urea that normally exits from the gel around the spacers to decrease.

Moreover, glass is more resistant to scratching than plastic.

Relative to the spacers according to the abovementioned WO 87/07719, the spacer according to the present invention also has the advantage that it comprises a single piece which is to be applied between the glass plates 1 and 2 without any need of fitting-in a light guide in the form of a piece of glass between a pair of pieces of plastic.

To improve the projection of excitation light from the side into the gel through the spacer of glass in accordance with the invention, at least a portion of the lateral surfaces of the spacer is polished.

The thickness of the spacers 3a and 3b can be selected to between 0.05 and 1.0 mm in view of the thickness of between 0.25 and 0.55 mm of electrophoresis gels used today for automatic nucleic acid sequencing.

In order for the glass to be of necessary strength, e.g. upon removal of the gel from the glass plates 1 and 2 after an electorphoresis run, the spacer according to the invention is preferably made of hardened glass.

It is not possible with today's technique to thermally harden glass with a thickness of between 0.05 and 1.0 mm. Instead, the spacers according to the invention are chemically hardened.

Chemical hardening of glass is normally carried out in that the glass pieces are lowered into a special salt bath in which an ion exchange takes place between the glass and the salt bath. Sodium in the glass is replaced by potassium or any other substance having larger atoms. Hereby, a compressive stress is built up in the surface layer of the glass, which is the desired effect. The chemical hardening process lasts between a few hours and a few days.

Thus, by means of the invention the problems with so far known spacers in gel cassettes for automatic sequencing, have been eliminated.

I claim:

1. An arrangement of a gel cassette, comprising:
   two glass plates; and
   at least two spacers disposed between said glass plates, wherein said spacers are arranged such that the thickness of the spacers defines a space for receiving an electrophoresis gel, said spacers being in the form of elongated, rectangular parallelepipeds, wherein at least one of the spacers is made of glass, and wherein a portion of the lateral surfaces of at least one spacer is polished.

2. An arrangement of a gel cassette, comprising:

two glass plates; and at least two spacers disposed between said glass plates, wherein said spacers are arranged such that the thickness of the spacers defines a space for receiving an electrophoresis gel, said spacers being in the form of elongated, rectangular parallelepipeds, and wherein at least one spacer is chemically hardened glass.

3. An arrangement according to claim 1 or 2, wherein the thickness of the spacer is between 0.05 and 1.0 mm.

4. A method for the detection of fluorophor labelled samples in a gel filled electrophoresis apparatus, comprising:

projecting an excitation light into a gel contained in said space in said arrangement of claim 1 or 2 from the side of said electrophoresis apparatus; and detecting the fluorophor labelled samples directly.

5. A method for the detection of fluorophor labelled samples in a gel filled electrophoresis apparatus, comprising:

projecting an excitation light into a gel contained in said space in said arrangement of claim 1 or 2 from the side of said electrophoresis apparatus; and detecting the fluorophor labelled samples directly, wherein the thickness of the spacer is between 0.05 and 1.0 mm.

* * * * *